Figure 1:
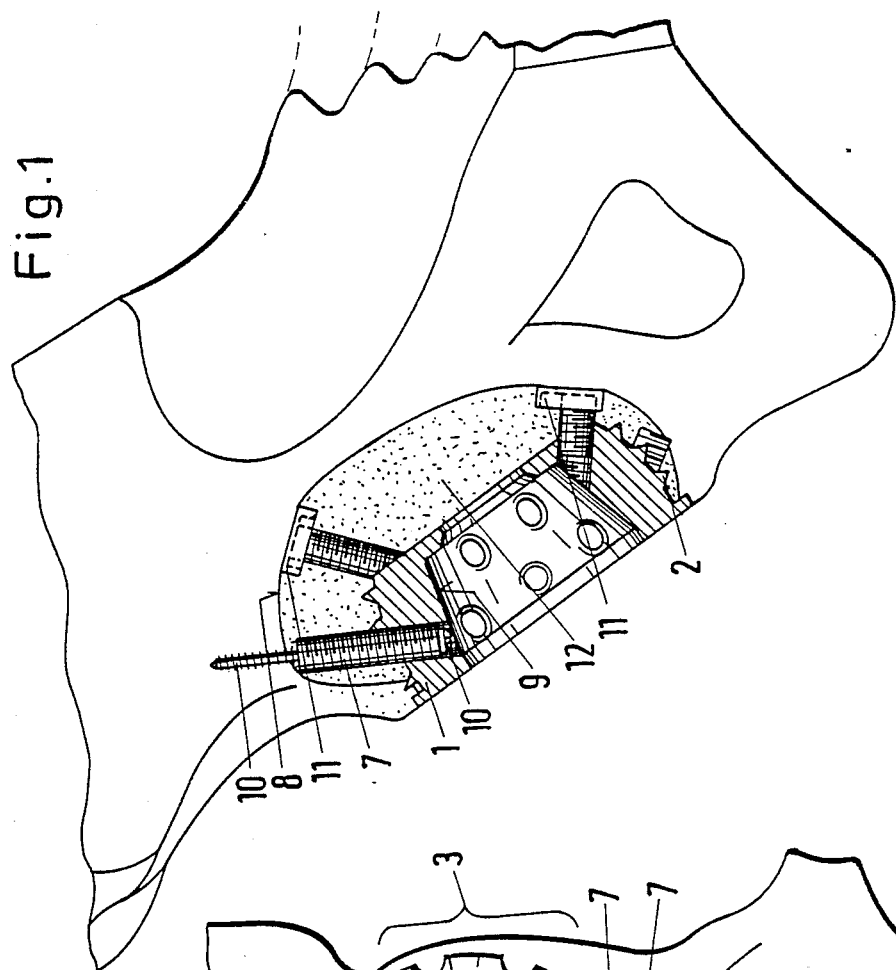

United States Patent [19]
Keller

[11] Patent Number: 4,936,856
[45] Date of Patent: Jun. 26, 1990

[54] HIP JOINT SOCKET PROSTHESIS

[75] Inventor: Arnold Keller, Kayhude, Fed. Rep. of Germany

[73] Assignee: Waldemar Link GmbH & Co., Hamburg, Fed. Rep. of Germany

[21] Appl. No.: 265,600

[22] Filed: Nov. 1, 1988

[30] Foreign Application Priority Data

Nov. 3, 1987 [DE] Fed. Rep. of Germany ... 8714635[U]

[51] Int. Cl.$^5$ .............................................. A61F 2/32
[52] U.S. Cl. .......................................................... 623/22
[58] Field of Search ............................................ 623/22

[56] References Cited

U.S. PATENT DOCUMENTS 3,740,769  6/1973  Haboush ................................ 623/22
4,456,005  6/1984  Lichty ..................................... 600/60
4,563,778  1/1986  Roche et al. ........................... 623/22
4,566,138  1/1986  Lewis et al. ............................ 623/22
4,792,337  12/1988 Müller .................................... 623/22

FOREIGN PATENT DOCUMENTS 2589059  4/1987  France ................................... 623/22

Primary Examiner—Randall L. Green
Assistant Examiner—Stephanie L. Iantorno
Attorney, Agent, or Firm—Chilton, Alix & Van Kirk

[57] ABSTRACT

Hip joint socket prosthesis with devices for anchoring to the bone. These comprise, for bridging an interspace between the socket surface and the bone, at least one support which projects from the socket surface and which is preferably extensible from the socket inside.

13 Claims, 2 Drawing Sheets

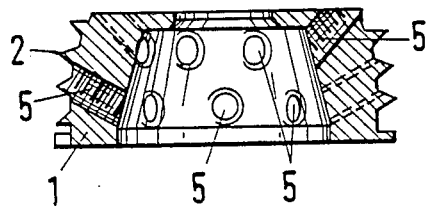
Fig. 3

Fig. 8 Fig. 9
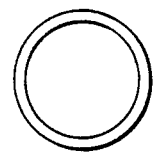 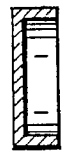

Fig. 10
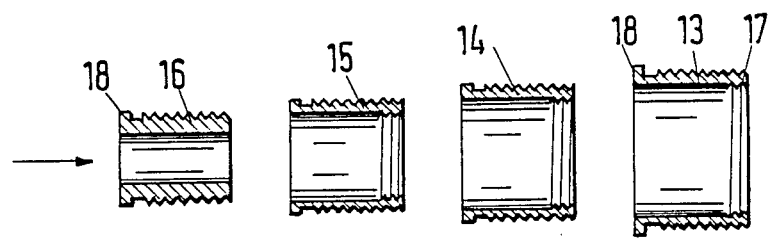
Fig. 11
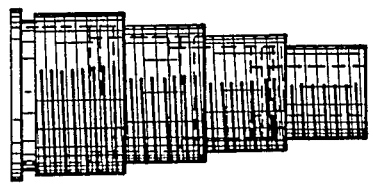

HIP JOINT SOCKET PROSTHESIS

DESCRIPTION

The invention relates to a hip joint socket prosthesis with devices for anchorage to the bone.

The known devices for cementless anchorage of socket prostheses in the bone such as, for example, threads on the outside of the mounting of a metal dish (DE-A 2,950,536) require that they can engage directly in the bone tissue surrounding the prosthesis without clearance essentially over the entire periphery. If, in the event of a re-operation, the acetabulum opening is widened by cranial displacement of the socket to be replaced in such a way that the insertion plane of the socket is no longer anatomically orbicular, but oval and the original concave spherical surface shape of the acetabulum has changed in such a way that a cavernous formation has developed below the ovally changed insertion plane of the socket, a new and stable provision of an acetabulum socket is in each case problematic. A further drilling-out of the acetabulum until restoration of an orbicular, semi-spherical concave form would have to be oriented to the size of the greatest oval extension and, moreover, also include the cavernous formation. This is mostly impossible in the direction transverse to the direction of the greatest extension of the insertion plane of the socket, including the cavernous formation, because of the absence of the necessary bone substance in this direction. A normal ilium wing does not provide the necessary extension, in particular in the ventral direction, so that such a procedure goes beyond the area available in the ventral direction and impairs the integrity of the ilium wing from caudal to cranial and thus renders it unstable. The excessive further bone loss is to be regarded as a further disadvantage of such a procedure. The ilium wing would thereby lose yet more stability and, likewise, measures which might be necessary in the future would be thereby considerably restricted.

In such cases a frequent measure is to fill the ovally shaped socket defect, including the cavern, with bone cement and to once more embed an artificial hip socket therein. In such a procedure the bone cement introduced not only prevents osseous reconstruction, but leads rather, as has been proven, to further destruction. At the same time the stability which can be achieved is to be regarded as very limited. A further known measure is the application of metal implants whose concave half-shells for receiving the artificial hip socket extend into the defect area of the acetabulum, and at whose edges, in the cranial and caudal directions, metal clips are attached and fixed by means of bone screws to the ilium wing. The stability of the possible fixation is problematic in this case too. Attempts are occasionally also made to fill the oval defect area, including the cavern, with autologous or homologous bone material, in order to achieve therein a renewed fixation of the artificial hip socket with simultaneous osseous reconstruction.

Of course, with this measure, the primary stability which can be achieved is to a great extent unreliable, and the success remains doubtful, even with long-term immobilization of the patient.

The invention is based on the object of providing anchoring devices for a hip joint socket prosthesis which, in these cases too, assure sufficient anchorage and do not exclude osseous reconstruction.

The solution according to the invention consists in providing, for the support of the prosthesis in the bone, at least one support which projects from the socket surface and which bridges the interspace between the socket and the bone tissue, without filling the cavern completely, so that a reconstruction of the natural bone tissue can take place gradually therein, which bone tissue is also generally able to participate subsequently in supporting the prosthesis.

The support is advantageously designed in such a way that, after the insertion of the socket, it can be extended from the latter, and this by actuation from the direction of the socket inside, since the outside is no longer accessible. For this purpose the socket and the support must be provided with co-operating holding devices which permit the subsequent displacement of the support and the transfer of the anchoring forces. In addition to other constructions, for example a bayonet holding device, the design of the prosthesis-side holding device as a threaded bore is especially suitable according to the invention, in which connection the support is designed as a pin with a corresponding thread provided at least at its socket-side end. The support may already be present in the holding device upon insertion of the socket; it is more expedient to provide a multiplicity of holding devices or threaded bores in the socket so that, after insertion of the socket, that holding device can be chosen which has the most favourable position in respect of the desired support. A multiplicity of such holding devices is therefore also expedient because, in general, one support does not suffice, but rather several of them must be used.

The design of the support as a pin to be inserted through the holding device opening from the inside of the socket limits its cross-sectional size and, thus, the size of the support area available on the bone surface. If a larger support area is desired, the bone-side end of the support can then be provided with a support plate which can be fixed, even before the implantation of the socket, at a suitable point on the bone surface or is attached on the outside of the socket in the region of the holding device to be used in such a way that, upon advancing the support, it connects with the latter.

With a view to as large a supporting area as possible of the support, the latter can be designed solid at the bone-side end. However, it can be advantageous to use a hollow support, in order to be able to guide through a bone screw.

After insertion of the socket the operating surgeon determines for each holding device to be used, by means of a depth gauge, the distance to the bone surface and, thus, the length of the support to be chosen. If it is desired to avoid this, then supports can be used according to the invention which consist of several sleeves which can be screwed telescopically into one another. According to a further feature these can, in the retracted state, have a common length which is not substantially greater than the thickness of the socket part containing the threaded bore, so that they can, upon insertion of the socket, already be contained therein and/or can be used for each distance between socket and bone.

Figure 2:
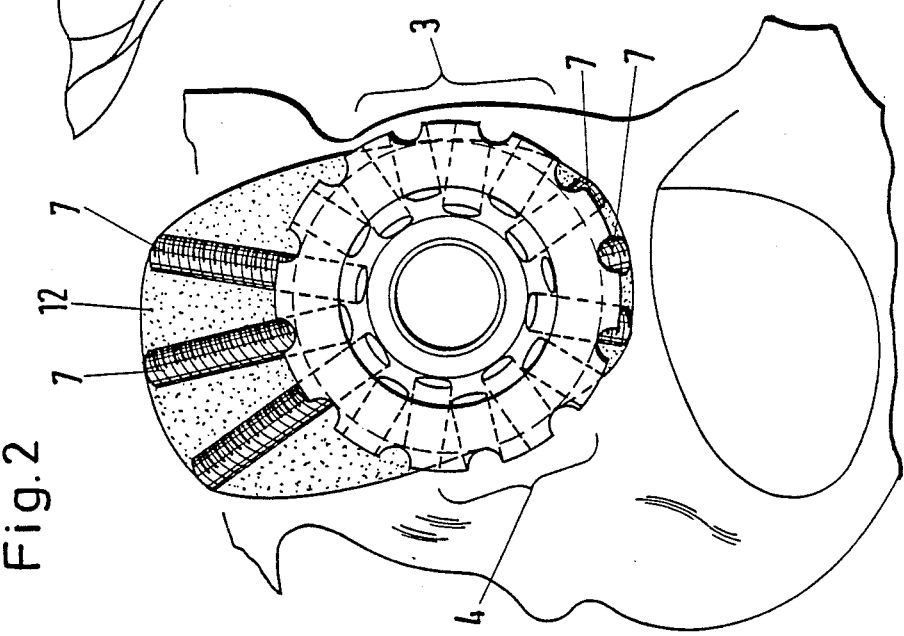
Figure 4:
Figure 5:
Figure 6:
Figure 7:

The invention will be described in greater detail below with reference to the drawing which illustrates advantageous exemplary embodiments and in which:

FIG. 1 shows a view of the implanted prosthesis and of the surrounding bone in the sagittal section, FIG. 2 shows an outer view in the direction of the socket axis, FIG. 3 shows an axial section through the socket, FIGS. 4 and 5 show two supports designed hollow or solid, FIGS. 6 and 7 show a side view of supports according to FIG. 4 of variable length, FIGS. 8 and 9 show a plan and sectional view of a support plate and FIGS. 10 and 11 show a telescope support and a sectional view of the telescope sleeves forming it.

According to FIGS. 1 and 2, in the area of the hip bone shown in dots, the acetabulum has been widened substantially ovally by cranial migration of a re-operated socket prosthesis to such an extent that the illustrated prosthesis part 1— which forms the metal mounting of a socket prosthesis which is to be supplemented by a plastic insert (not shown)— with its anchoring projections 2 provided over the periphery and designed as threads only directly reaches the bone tissue laterally in zones 3 and 4, which is inadequate in the case of cementless anchoring.

As can be seen above all in FIGS. 2 and 3, the mounting is provided with a multiplicity of threaded bores 5 which are uniformly distributed over the periphery in several rows. The bores lie in common planes with the socket axis and are arranged at an angle such that the extension of their center axes points approximately to the joint midpoint. The angle included with the socket axis is about 50° to 90° in the row closer to the opening and about 35° to 50° in the row further from the opening. In each case about 6 to 10, i.e. 8 holes, are distributed over the periphery in each row. Altogether, the support angles lie advantageously between 35° and 90° to the socket axis.

Headless pins are provided as the supports, which pins can, according to FIGS. 4 to 7, be hollow or solid, have a variable length and contain, at one end, a slot 6, a hexagonal socket or the like for attachment of a turning tool. According to FIG. 2 three such supports 7 each pass through the outer surface of the prosthesis, the length of the supports being chosen such that, on the one hand, they project up to the bone surface 8 and may also be pressed slightly into the latter and, on the other hand, project inwards but not beyond the inner surface 9 provided for receiving the insert.

Whereas the supports shown in FIG. 2 bear against the bone surface without further aids and are fixed thereby, in one of the supports appearing in FIG. 1 a bone screw 10 is provided which passes through the hollow-designed support. In two other supports support plates 11 are provided for reducing the surface pressure acting on the bone, which support plates can be of the type shown in FIGS. 8 and 9 and are held between the bone surface 8 and the supports 7 simply by clamping. Instead of these, special connecting members can also be provided for firm connection to the supports.

The cavity 12 between the prosthesis and bone surface 8 is lined with bone material in order to promote a reconstruction of the bone tissue in this area, which bone tissue, depending on the rate of growth, participates after several weeks to months in transferring strength to the prosthesis. Until that time the supports ensure a primary functional and exercise stability.

The telescopically constructed support according to FIGS. 10 and 11 consists of several telescope sleeves 13, 14, 15, 16, of which the largest 13 has an external thread corresponding to the threaded bores of the socket and an internal thread corresponding to the external thread of the next smaller telescope sleeve 14, etc. up to the smallest sleeve 16 which has no internal thread but can have a bore for receiving a bone screw and also a hexagonal socket for a turning tool. The three larger sleeves have on the inside, at that end which will later point outwards, a threadless collar 17 while, at the other end, an outer threadless collar 18 is provided which cooperates with the collar 17 in such a way that no sleeve can be screwed outwards from the next larger one.

In the initial stage all the sleeves lie inside one another so that the overall length corresponds to the length of each of the sleeves shown and is not greater, or not substantially greater, than the length of a bore 5 of the prosthesis receiving them. If, using a suitable tool, the sleeve 16 is now turned, then the sleeves shift successively outwards in the direction of the arrow (FIG. 10) until the sleeve 16 has reached the bone surface 8.

Suitable devices can be provided, both for the threaded bolts 7 and for the telescope supports 13 to 16, for fixing the rotational position achieved, which devices can be taken from the prior art.

After the anchoring of the prosthesis part 1, the insert forming the articular surface can be inserted.

The prosthesis part forming the holding devices 5 for the supports can be of any desired type. It will be seen, however, from the exemplary embodiments that the invention can be used with particular advantage in those socket prostheses which consist of a mounting part 1 of rigid material, which then contains the holding devices, and a special insert.

In the examples the supports are used for bridging a space between the prosthesis surface and the bone surface. There can be cases in which they are also used when such a space does not exist, that is to say simply for the purposes of better anchorage in the bone, in which connection the support used, which can be pointed at the end, penetrates slightly into the bone surface without, however, transferring tensile forces in the manner of a bone screw.

I claim:

1. An acetabular prosthesis to be supported in a cavity in the hip bone, comprising:
   a socket member having means (2) for anchoring the socket member to the bone, an outer surface for facing the portion of the bone defining the cavity, and an inner surface (9) for receiving a prosthesis insert;
   at least one elongated support (7,13–16) adapted to be coupled to the socket member and configured to extend outwardly a variable length from the outer surface into the cavity;
   said support having means accessible from the socket inner surface for selectively adjusting the variable length after the socket member has been anchored to the bone, thereby bridging any interspace that may exist between the socket member outer surface and said portion of the bone defining the cavity.

2. The prosthesis as claimed in claim 1, wherein the socket includes a plurality of threaded bores (5) and each support (7,13–16) is in the form of a pin which is at least partially threaded.

3. The prosthesis as claimed in claim 1, wherein the support (7,13–16) has an outer end remote from the base member and is provided, at the outer end, with a support plate (11).

4. The prosthesis as claimed in claim 1 wherein the support (7,13-16) is hollow for receiving a bone screw (10).

5. The prosthesis as claimed in claim 1 wherein the support comprises several sleeves (13-16) which can be screwed telescopically into one another.

6. The prosthesis as claimed in claim 5, wherein the socket has a thickness and includes at least one threaded bore and the telescope sleeves (13-16), in the retracted state, have a common length which is not substantially greater than the thickness of the socket part (1) containing the threaded bore (5).

7. An acetabular prosthesis to be anchored against a hip bone portion that includes a bone cavity, comprising:
- a rigid base member (1) having an outer surface including means (2) for directly rigidly engaging some of the bone (3,4) that forms said bone portion, while a portion of said outer surface is exposed to said cavity (12) and spaced from the bone (8), and an inner surface (9) defining a socket for receiving an insert member; and
- at least one support element (7,13-16) adapted to be coupled to the socket member, said support element being accessible from the inner surface and configured to extend outwardly a variable length from the outer surface into the cavity, whereby the variable length may be selectively adjusted after the socket member has been anchored to the bone.

8. The prosthesis of claim 7, wherein the base member has at least one threaded through bore (5) and one of the support elements is in the form of a pin (7, 13-16) having a threaded portion engaging said threaded bore.

9. The prosthesis of claim 8, wherein the base member includes a multiplicity of threaded bores.

10. The prosthesis of claim 7, wherein at least one support element is hollow for receiving a bone screw (10) passing from the base member into the bone portion.

11. The prosthesis of claim 7, wherein the support element includes a transversely oriented plate portion (11) for bearing against said bone portion.

12. The prosthesis of claim 7, wherein the support element includes several sleeves (13-16) that can be telescopically screwed into one another.

13. The prosthesis of claim 12, wherein the base member has a thickness and includes a bore to which a support element is coupled, and the sleeves of the support element have a telescopically retracted condition in which the support element has an overal length which is not substantially greater than the thickness of the base member.

* * * * *